United States Patent [19]

Ogura et al.

[11] Patent Number: 5,364,533
[45] Date of Patent: Nov. 15, 1994

[54] PROCESS FOR SEPARATING SERUM AND PLASMA

[75] Inventors: Shinji Ogura; Hiroshi Okada; Shizuo Uno; Takashi Iida; Hiromoto Asai; Masayasu Kurono; Kiichi Sawai, all of Nagoya, Japan

[73] Assignee: Sanwa Kagaku Kenkyusho Co., Ltd., Nagoya, Japan

[21] Appl. No.: 913,169

[22] Filed: Jul. 14, 1992

[30] Foreign Application Priority Data

Jan. 10, 1992 [JP] Japan ................. 4-3215

[51] Int. Cl.$^5$ .................. B01D 61/00; B01D 39/06
[52] U.S. Cl. ..................... 210/645; 210/504; 210/505; 210/767; 436/177
[58] Field of Search ............ 210/503, 504, 505, 650, 210/508, 509, 645, 767, 782, 929, 435, 445, 446, 496; 436/169, 170, 177, 178; 422/56, 57, 58; 530/396

[56] References Cited

U.S. PATENT DOCUMENTS

| | | | |
|---|---|---|---|
| 3,493,503 | 2/1970 | Mass . | |
| 3,814,079 | 6/1974 | Le Roy, Sr. | 210/359 |
| 4,426,295 | 1/1984 | Evans et al. | 210/772 |
| 4,477,575 | 10/1984 | Vogel et al. | 210/509 |
| 4,776,959 | 10/1988 | Kasai et al. | 210/490 |
| 4,810,394 | 3/1989 | Masuda | 210/767 |
| 4,816,224 | 3/1989 | Vogel et al. | 210/767 |
| 4,936,993 | 6/1990 | Nomura | 210/505 |
| 4,985,543 | 1/1991 | Sugita et al. | 530/396 |
| 5,000,854 | 3/1991 | Yang | 210/638 |
| 5,064,541 | 11/1991 | Jeng et al. | 210/767 |
| 5,066,401 | 11/1991 | Müller et al. | 210/500.35 |
| 5,130,231 | 7/1992 | Kennedy et al. | 436/170 |
| 5,135,719 | 8/1992 | Hillman et al. | 210/503 |
| 5,186,843 | 2/1993 | Baumgardner et al. | 210/767 |
| 5,244,578 | 9/1993 | Ohnishi et al. | 210/650 |

FOREIGN PATENT DOCUMENTS

| | | |
|---|---|---|
| 295526 | 12/1984 | European Pat. Off. . |
| 0283663 | 9/1988 | European Pat. Off. . |
| 305803 | 3/1989 | European Pat. Off. . |
| 457183 | 11/1991 | European Pat. Off. . |
| 4-187206 | 7/1992 | Japan . |
| 2232599 | 12/1990 | United Kingdom . |

OTHER PUBLICATIONS

Patent Abstract of Japan, vol. 10, No. 119 (P-453) 6 May 1986 of JP-A-60-247163 (Tokyo Boseki KK) 6 Dec. 1985.

Primary Examiner—Robert A. Dawson
Assistant Examiner—Sun Uk Kim
Attorney, Agent, or Firm—Armstrong, Westerman, Hattori, McLeland & Naughton

[57] ABSTRACT

A process for separating and recovering serum and plasma components from a whole blood sample including passing a whole blood sample through a separating filter formed of a blood cell separating layer composed mainly of fibers impregnated with a coating agent. A device includes a blood collector having a needle at one end and a blood suction means at the other end, and a separating filter including a blood cell separating layer, the filter being provided in the intermediate zone of the blood collector, whereby a whole blood sample sucked through the needle by depressurizing the blood suction means is passed through the separating filter.

2 Claims, 5 Drawing Sheets

PROCESS FOR SEPARATING SERUM AND PLASMA

The present invention relates to a process and device for easily and efficiently separating and recovering serum or plasma components from whole blood. The present invention is used for separating and recovering serum or plasma components from blood samples when clinical chemistry analyses, bedside and other real-time assays are emergently needed.

A conventionally, or even currently, available, typical method of separating serum or plasma from whole blood is centrifuging. According to this centrifuge method, blood usually collected through an injector, which may or may not contain an anticoagulant, is placed in a tubular vessel, in which it is separated into cellular components and other cell-free constituents under the action of a gravity of about 650 to 1500 G. The separated cell-free constituents are used for a variety of clinical assays and tests available for various diagnoses and therapies. On the other hand, reagents themselves having a mechanism capable of separating or serum from whole blood have been developed with the progress of dry chemistry reagents, opening a new way for emergent assays and rapid bedside tests.

For instance, Vogel et al in U.S. Pat. No. 4,477,575 discloses a testing paper including a filter paper form of glass fiber layer for collecting blood cells, which is made integral with a reagent-reacting layer. As set forth therein, serum or plasma separated from a slight volume of whole blood (a few to 30 $\mu$l) through a blood cell separating region moves from there into the reagent reacting region in close contact with the blood cell separating region, where it reacts with the reagent to make a real-time assay of serum or plasma. Lon R. Stover et al in EP-A-295526 discloses a blood cell separating region formed of a filter paper form of bibulous matrix comprising a lectin having a red blood cell agglutinizing activity and a bibulous material (hydrophilic organic powders, cellulosic material, etc.) and teaches a method of using this to separate serum and plasma components from a whole blood sample and guide them to the reaction region.

The centrifuge or other method is suitable for large laboratories that assay a multitude of blood samples, and for institutions, such as hospitals, not requiring the assay results of (usually 1 to 10) tests in a matter of minutes. However, many small or private medical offices do not have such a costly, special blood separator on site. Therefore, the whole blood must be sent elsewhere for separation and assay. As a result, the assay results are not available in minutes but in hours or days. In some cases, the whole blood, when stored as such in days, would produce an assay error or make its assay impossible for hemolysis or other reasons. For patients with infectious diseases, much more care should be taken of disposal of the test vessel after use than of the operation of the centrifuging device.

According to the methods disclosed in U.S. Pat. No. 4,477,575 and EP-A-295526, the problems mentioned above may be solved, because the blood cell separating regions are made integral with the reagent reacting regions. However, because of relying on dry chemistry reactions, it is not possible to prepare reagent reaction regions for immunoassay. As regards the separated serum and plasma components, different reagent reaction regions are needed for individual tests. However, again, all reagent reaction regions are not prepared for all numerous tests. In addition, the object of these methods is to allow slight volumes of blood to react with slight volumes of reagents; in other words, it is impossible to obtain serum and plasma independently. Even when some modifications are made to these methods, e.g., even when a plurality of a filter form of blood cell separating regions are stacked up to prepare a separating layer, it is impossible to obtain serum and plasma due to hemolysis or other phenomenon.

It is therefore a main object of this invention to provide a simple and rapid process for separating serum and plasma components from a whole blood sample for the purpose of real-time tests such as emergent clinical, chemical analyses and bedside examinations. Another object of this invention is to provide a simple device to simply and rapidly separate serum or plasma components from body fluids, e.g., whole blood for about a few to ten tests.

As a result of investigating various fibrous materials in terms of their capabilities of separating blood cells from whole blood, we have found that they are unsuitable for obtaining serum or plasma in amounts well enough for about a few to ten tests, because hymolysis is likely to occur during separation. From the relations between the type, size and density of fibrous material and the coating material therefor, however, we have now discovered that serum or plasma can be efficiently and instantaneously separated from whole blood with a blood cell-separating layer comprising nonwoven fabric, cellulose or glass fibers and a coating agent, said fibers having a length lying in the range of 100 to 3000 $\mu$m and a density of 50 to 250 mg/cm$^3$.

SUMMARY OF THE INVENTION

According to one aspect of this invention, there is provided a process for separating and recovering serum and plasma components from a whole blood sample, which comprises passing said whole blood sample through a separating filter formed of a blood cell-separating layer composed mainly of cellulose or glass fibers impregnated with a coating agent.

Preferably, the fibers have a diameter of 0.8 to 2.5 $\mu$m, a length of 100 to 3000 $\mu$m and a density of 100 to 300 mg/cm$^3$.

Preferably, the coating agent is a surface active agent or agents having wetting power, which may or may not contain a nonblood group specific lectin that interacts on blood. This surface active agent, for instance, may be polyethylene glycol hereinafter PEG for short)or docusate sodium.

According to another aspect of this invention, there is provided a device for separating and recovering serum and plasma from a whole blood sample, which comprises a blood collector having a needle at one end and a blood sucker at the other end, and a separating filter including a blood cell-separating layer, said filter being provided in the intermediate zone of said blood collector, whereby said whole blood sample sucked through said needle by depressurizing said blood sucker is passed through the said separating filter.

According to the third aspect of this invention, there is provided a device for separating and recovering serum and plasma from a whole blood sample, which comprises an extruder for extruding said whole blood sample from within under pressure and a separator connected to said extruder and receiving a separating filter including a blood cell separating layer therein, whereby said whole blood sample is passed from said extruder through said separator.

DETAILED EXPLANATION OF THE INVENTION

According to this invention, the coating agent is a surface active agent having wetting power, for instance, polyethylene glycol or docusate sodium. In particular, it is desired that polyethylene glycol be used in the form of a mixture with a polyacrylic ester derivative.

According to this invention, it is found that the coating agent produces a sufficient effect at a concentration of 0.01 to 10%. If desired, the coating agent may additionally contain a lectin that interacts on blood. To this end any lectin is used, if it is a nonblood group specific one. Thus, especially when the coating agent contains the nonblood group specific lectin, it is well capable of separating serum and plasma from whole blood at a reduced concentration.

Of the polyacrylic ester derivatives, particular preference is given to poly(butyl acrylate) (hereinafter PBA for short), poly(methyl acrylate) (PMA) and poly(ethyl acrylate) (PEA). With glass fibers containing these derivatives together with PEG, it has been found that hundreds of μl of serum or plasma can be easily separated from about 1 ml of a whole blood sample in minutes. In addition, it has been found that the provision of the lectin-impregnated layer makes that separation more efficient.

The polyacrylic ester derivatives are preferably used in the form of a mixture of (a) PBA and (b) PMA or PEA. More preferably, a mixture of (a), (b) and (c) PEG is used at a ratio of (10–20):(1–4):(1–4) and in a total amount of 2 to 3%, because particularly favorable separation of blood cells is then achieved.

Any blood cell agglutinizing agent may be used for the blood cell separating layer and lectin-impregnated layer, if it is a nonblood group specific one, and produces a sufficient effect in a slight amount as low as 0.01 to 0.005% by weight. The lectins used, by way of example, Abrus precatorius (abrin, Jequirty bean), Bauhinia purpurea (camels foot tree), Caragana arborescens (Siberian pea tree), Codium fragile (Green marine algae), Concanavalin A (Jack bean), Glycine max (Soybean), Lathyrus odoratus (Sweet Pea), Lens culinaris (Lentil), Limulus polyphemus (Horseshoe crab, Limulin), Lycopersicon esculentum (Tomato), Maclura pomifera (Osage orange), Mycoplasma gallisepticum, Petseau americana (Avacado), Phaseolus coccineus sativum (garden pea), Psophocarpus tetragonolobus (winged bean), Ricinus communis (Castor bean), Solanum tuberosum (Potato), Triticum vulgaris (Wheat germ), Vicia faba (faba bean, broad bean), Vigna radiata (Mung bean), Viscum album (European bean) and Wisteria floribunda (Japanese wisteria).

EXAMPLES

The present invention will now be explained more specifically but not exclusively with reference to several examples.

Production Example 1

Glass fibers having diameters of 0.8 to 2.5 μm are pulverized to lengths of 100 to 3000 μm. The pulverized glass fibers are suspended in a polyethylene glycol solution, then packed in a conical vessel at a density of 100 to 300 mg/cm$^3$ and finally dried to form a separating filter.

Production Example 2

Glass fibers having diameters of 0.8 to 2.5 μm are pulverized to lengths of 100 to 3000 μm. The pulverized glass fibers are suspended in a docusate sodium solution, then packed in a conical vessel at a density of 100 to 300 mg/cm$^2$ and finally dried to form a separating filter.

Production Example 3

Glass fibers having diameters of 0.8 to 2.5 μm are pulverized to lengths of 100 to 3000 μm. The pulverized glass fibers are suspended in a mixed solution of polyethylene glycol and Glycine max (Soybean) lectin, then packed in a conical vessel at a density of 100 to 300 mg/cm$^3$ and finally dried to form a separating filter.

Production Example 4

Glass fibers having diameters of 0.8 to 2.5 μm are pulverized to lengths of 100 to 3000 μm. The pulverized glass fibers are suspended in a polyethylene glycol solution. After that, the suspension is packed in a cylindrical vessel with a needle connected to it at a density of 100 to 300 mg/cm$^3$, followed by drying. Finally, a rubber plug is tightly put in the upper portion of the vessel to form a vacuum type of serum/plasma separating device.

Comparative Production Example 1

Similar glass fibers as used in the above examples are suspended under agitation in a polyethylene glycol-free solution, and then packed in a conical vessel at a density of 100 to 300 mg/cm$^3$. Subsequent drying gives a sample for comparative testing.

The following tests were conducted to find whether or not there was a significant difference between the volumes of the components in serum or plasmas actually separated from whole blood by each of the separating filters and conventional centrifuging.

Test Examples

Hare's fresh blood was added dropwise to each of the separated filter obtained in Production Example 1 and the control sample obtained in Comparative Production Example 1 to separate plasma from it. The volume and degree of hemolysis of the collected plasma and the time of separation were measured. The results are set out below.

| Test No. | Degree of Hemolysis | | Time of Sepn. (min.) | | Amount (μl) | |
|---|---|---|---|---|---|---|
| | PE1 | CPE | PE1 | CPE | PE1 | CPE |
| 1 | — | — | 140 | 210 | 100 | 30 |
| 2 | — | — | 150 | 260 | 90 | 40 |
| 3 | — | + | 120 | 290 | 80 | NR |
| 4 | — | — | 130 | 240 | 70 | 40 |
| 5 | — | — | 150 | 660 | 100 | 35 |
| 6 | — | + | 120 | 260 | 110 | NR |
| 7 | — | + | 125 | 210 | 90 | NR |
| 8 | — | — | 135 | 660 | 110 | 30 |
| 9 | — | — | 145 | 210 | 90 | 25 |
| 10 | — | + | 125 | 660 | 70 | NR |
| * | 10/10 | 6/10 | 134 (av.) | 366 (av.) | 91 | 33 |

*: Not Hemolyzed Portion
PE: Production Example
CPE: Comparative Production Example
NR: Not Recovered

Test Example 1—Determination of Glucose

For the determination of glucose, use was made of three whole blood samples having different glucose concentrations, one subjected to centrifuging (for control) and the remaining two to serum separation with the serum separating column according to this invention. In all the cases, the concentrations of glucose were measured with a commercially available reagent (enzyme). The results are set out below.

| Test No. | Sample I C | Sample I I | Sample II C | Sample II I | Sample III C | Sample III I | |
|---|---|---|---|---|---|---|---|
| 1 | 110 | 113 | 237 | 242 | 528 | 536 | μmol/l |
| 2 | 99 | 110 | 242 | 241 | 529 | 539 | mol/l |

C: Control, and I: Invention

Test Example 2—Determination of 3-Hydroxbutyric Acid

For the determination of 3-hydroxybutyric acid, use was made of three whole blood samples having different 3-hydroxybutyric acid concentrations, one subjected to centrifuging (for control) and the remaining two to serum separation with the serum separating column according to this invention. In all the cases, the concentrations of glucose were measured with a commercially available reagent (enzyme). The results are set out below.

| Test No. | Sample I C | Sample I I | Sample II C | Sample II I | Sample III C | Sample III I | |
|---|---|---|---|---|---|---|---|
| 1 | 89 | 91 | 105 | 110 | 187 | 186 | μmol/l |
| 2 | 90 | 93 | 112 | 110 | 185 | 185 | μmol/l |

C: Control, and I: Invention

Test Example 3—Determination of Total Bile Acids

For the determination of total bile acids, use was made of three whole blood samples having different total bile acids concentrations, one subjected to centrifuging (for control) and the remaining two to serum separation with the serum separating column according to this invention. In all the cases, the concentrations of glucose were measured with a commercially available reagent (enzyme). The results are set out below.

| Test No. | Sample I C | Sample I I | Sample II C | Sample II I | Sample III C | Sample III I | |
|---|---|---|---|---|---|---|---|
| 1 | 10.5 | 10.9 | 25.0 | 26.1 | 51.9 | 50.9 | mg/dl |
| 2 | 10.6 | 10.9 | 25.5 | 25.8 | 51.0 | 52.2 | mg/dl |

C: Control, and I: Invention

Test Example 4—Determination of GPT

For the determination of GPT, use was made of three whole blood samples having different GPT concentrations, one subjected to centrifuging (for control) and the remaining two to serum separation with the serum separating column according to this invention. In all the cases, the concentrations of GPT were measured with a commercially available reagent (enzyme). The results are set out below.

| Test No. | Sample I C | Sample I I | Sample II C | Sample II I | Sample III C | Sample III I | |
|---|---|---|---|---|---|---|---|
| 1 | 40 | 41 | 109 | 112 | 318 | 315 | IU |
| 2 | 42 | 38 | 113 | 108 | 312 | 312 | IU |

C: Control, and I: Invention

Production Example 5

Glass fibers GB100R (Toyo Roshi Co., Ltd.) having an average diameter of 0.5 to 2.5 m are impregnated with a 5.5% methanol solution containing PBA, PMA and polyethylene glycol at 12:2:1; followed by drying. The dried fibers are finely pulverized, packed in a column of 70 mm in inner diameter and 30 mm in height, and impregnated with a 0.01% saline solution of *Glycine max* (Soybean) lectin. Finally, Nonwoven fabric QUINOCLOTH K70 (Honshu Seishi Co., Ltd.), dried at room temperature for about 1 hour and cut to the same size, was put on the thus impregnated fibers to form a mini-column.

The following tests were conducted to find whether or not there was a significant difference between the volumes of the components in serum or plasmas actually separated from whole blood by the mini-column obtained in Ex. 5 and conventional centrifuging.

Test Example 5—Determination of Glucose In Serum

For the determination of glucose, use was made of three whole blood samples having different glucose concentrations, one subjected to centrifuging (for control) and the remaining two to serum separation with the serum separating column according to this invention. In all the cases, the concentrations of glucose were measured with a commercially available reagent (enzyme). From the results set out in Table 1, it is noted that there is no significant difference between the samples.

| Test No. | Sample I C | Sample I I | Sample II C | Sample II I | Sample III C | Sample III I | |
|---|---|---|---|---|---|---|---|
| 1 | 241 | 242 | 528 | 536 | 808 | 811 | μmol/l |
| 2 | 242 | 241 | 529 | 539 | 808 | 816 | μmol/l |

C: Control, and I: Invention

Test Example 6—Determination of 3-Hydroxbutyric Acid In Serum

For the determination of 3-hydroxybutyric acid, use was made of three whole blood samples having different 3-hydroxybutyric acid concentrations, one subjected to centrifuging (for control) and the remaining two to serum separation with the serum separating column according to this invention. In all the cases, the concentrations of glucose were measured with a commercially available reagent (enzyme). From the results set out in Table 2, it is noted that there is no significant difference between the samples.

TABLE 2

| Test No. | Sample I C | Sample I I | Sample II C | Sample II I | Sample III C | Sample III I | |
|---|---|---|---|---|---|---|---|
| 1 | 89 | 91 | 109 | 110 | 187 | 186 | μmol/l |
| 2 | 90 | 93 | 112 | 110 | 185 | 185 | mmol/l |

C: Control, and I: Invention

Test Example 7—Determination of Total Bile Acids

For the determination of total bile acids, use was made of three whole blood samples having different total bile acids concentrations, one subjected to centrifuging (for control) and the remaining two to serum separation with the serum separating column according to this invention. In all the cases, the concentrations of glucose were measured with a commercially available reagent (enzyme). From the results set out below in Table 3, it is noted that there is no significant difference between the samples.

TABLE 3

| Test No. | Sample I C | Sample I I | Sample II C | Sample II I | Sample III C | Sample III I | |
|---|---|---|---|---|---|---|---|
| 1 | 10.5 | 10.9 | 17.2 | 17.8 | 33.1 | 33.4 | mg/dl |
| 2 | 10.6 | 10.9 | 17.2 | 18.1 | 33.0 | 33.6 | mg/dl |

C: Control, and I: Invention

BRIEF DESCRIPTION OF THE DRAWINGS

In what follows, some embodiments of the serum/plasma separating device according to this invention will be explained more specifically but not exclusively with reference to the accompanying drawings, in which.

DETAILED EXPLANATION OF THE PREFERRED EMBODIMENTS

Figure 1:
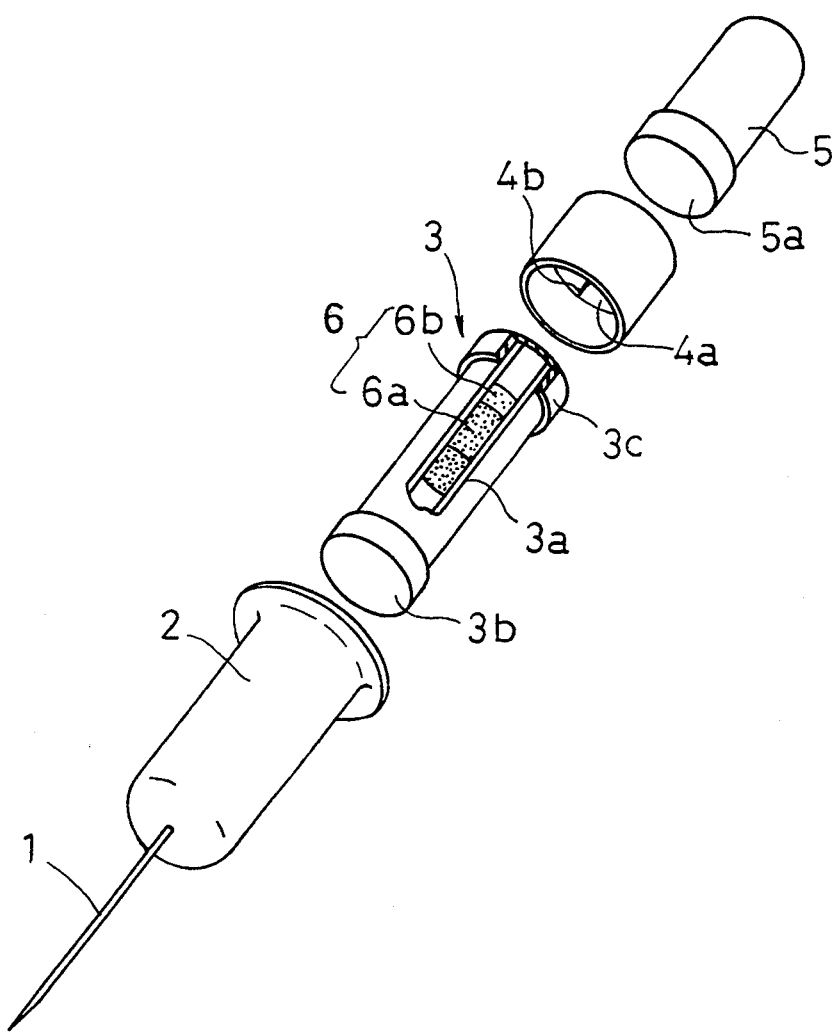
FIG. 1 is a perspective view of the first embodiment of the serum/plasma separating device according to this invention.
Figure 2:
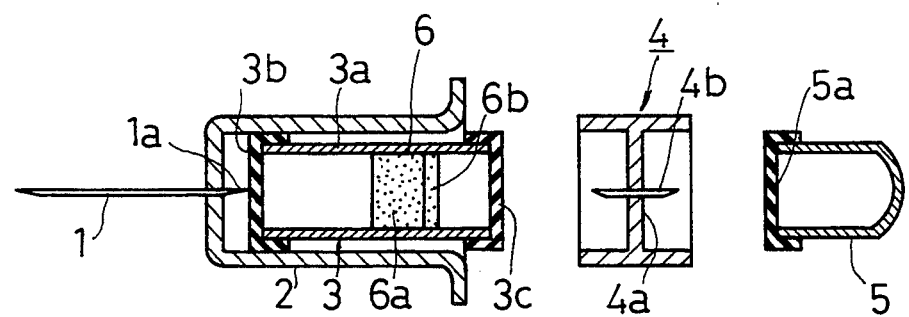
FIG. 2 is a sectional view of the first embodiment.

Referring now to FIGS. 1 and 2, there is the first embodiment of the serum/plasma separating device according to this invention. As illustrated, the separating device is built up of a bottomed, outer tube 2 including a needle 1 at one end, a tubular blood collector 3 fitted into the outer tube 2 and depressurized substantially to vacuum, a connector 4 fitted into the rear end of the blood collector 3 and a tubular form of separated fluid collector 5 fitted into the rear end of the connector 4 and depressurized substantially to vacuum. When not in use, the blood collector 2, the connector 4 and the separated fluid collector 5 remain separated from each other.

The outer tube 2 is in a bottomed, cylindrical form, and the needle 1 for collecting blood is fixed through the front end of the outer tube 2, said needle 1 being inwardly bent at its rear end. The blood collector 3 is built up of a cylindrical body 3a open at both ends, and nonpermeable plug members 3b and 3c formed of rubber material, with which both ends of the body 3a are tightly closed. Within the collector body 3a there is a blood cell separating filter 6, which is of a double-layer structure comprising a fibrous material layer 6a for separating blood cells from a whole blood sample and a blood cell agglutinizing agent layer 6b impregnated with lectin. Note that this blood cell agglutinizing agent layer 6 may be dispensed with.

The connector 4 is in a cylindrical form having a partition 4a substantially at its center, and an axially double-headed, hollow, connecting needle 4b is fixedly passed through the central region of the partition 4a. The separated fluid collector 5 is in a bottomed, cylindrical form and has an opening tightly closed by a nonpermeable plug member 5a formed of rubber material. This collector 5 is depressurized substantially to vacuum.

How to use this separating device will now be explained. For collecting blood, the needle 1 is first stuck in the blood vessel under the skin, and the blood collector 3 is then forced into the outer tube 2 to stick the inward needle 1a into the plug member 3b. Consequently, the blood is vacuum-sucked in the blood collector 3. After the required volume of blood has been collected, the needle 1 is removed from the skin. Thereafter, the collector 5 is pressed against the rear portion of the blood collector 3 through the connector 4, so that the connecting needle 4b can break through the plug member 3c of the blood collector 3 and the plug member 5a of the separated fluid collector 5. Consequently, the blood can be vacuum-sucked from the blood collector 3 into the separated fluid collector 5 through the blood cell separating filter 6. In the meantime, the blood is separated into serum and plasma components through the filter 6, which are then pooled in the separated fluid collector 5.

It has been confirmed that this method enables hundreds of $\mu l$ of serum and plasma to be obtained from about 1 ml of a whole blood sample. This amount of serum and plasma enables as many as 10 or more blood tests to be done simultaneously with blood-collecting.

Figure 3:
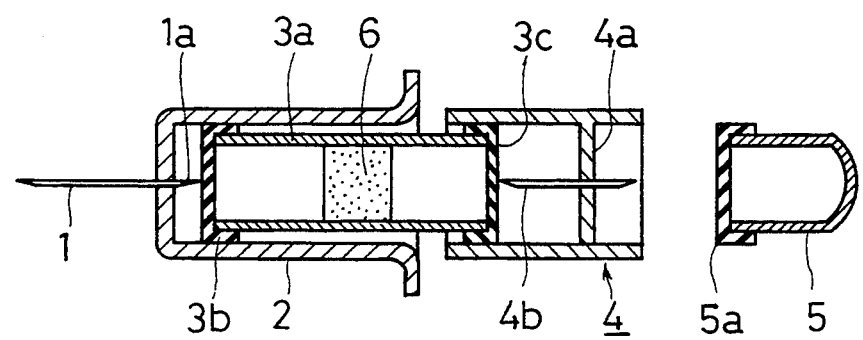
FIG. 3 is a sectional view of the second embodiment of the serum/plasma separating device according to this invention.

Referring to FIG. 3, there is shown the second embodiment of the separating device according to this invention. In the first embodiment, the blood collector 3 is separated from the connector 4 and the fluid collector 5 prior to use. In the second embodiment, however, these parts are made integral with each other. More specifically, while the needle 1 remains stuck in the blood vessel, the fluid collector 5 is forced into the outer tube 2 together with the blood collector 3.

Figure 4:
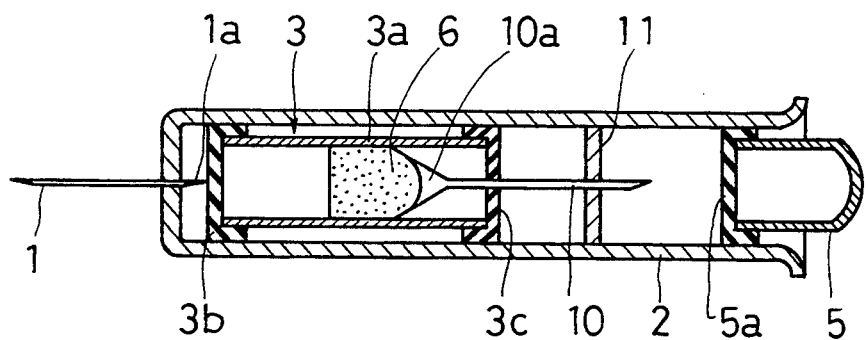
FIG. 4 is a sectional view of the third embodiment of the serum/plasma separating device according to this invention.

Referring to FIG. 4, there is shown the third embodiment of the separating device according to this invention. As illustrated, an outer tube 2 is provided at its rear end with an extention, in which a separated fluid collector 5 is slidably pre-fitted. A hollow needle 10 is fixed at its one end in a blood collector 3 and extends from there through the rear end of the blood collector 3. The tip portion of this hollow needle 10 is supported by a partition 11 and located in opposition to the fluid collector 5.

At the rear end of the needle 10 there is integrally provided a funnel form of filter support plate 10a, which supports and keeps the rear part of a filter from movement. According to this arrangement, as the fluid collector 5 is forced into the outer tube 2 for collecting blood, the hollow needle 10 break through the plug members 3b and 5a of the collectors 3 and 5, so that the blood can be vacuum-sucked into the blood collector 3 and the serum and plasma separated through the filter 6 can be sucked into the collector 5. This third embodiment of the separating device according to this invention enables serum and plasma to be separated and recovered from a whole blood sample simultaneously with blood sampling. Since the filter 6 is kept from co-movement by the support plate 10a during vacuum suction, the serum and plasma are more efficiently separated and recovered from the blood sample.

Figure 5:
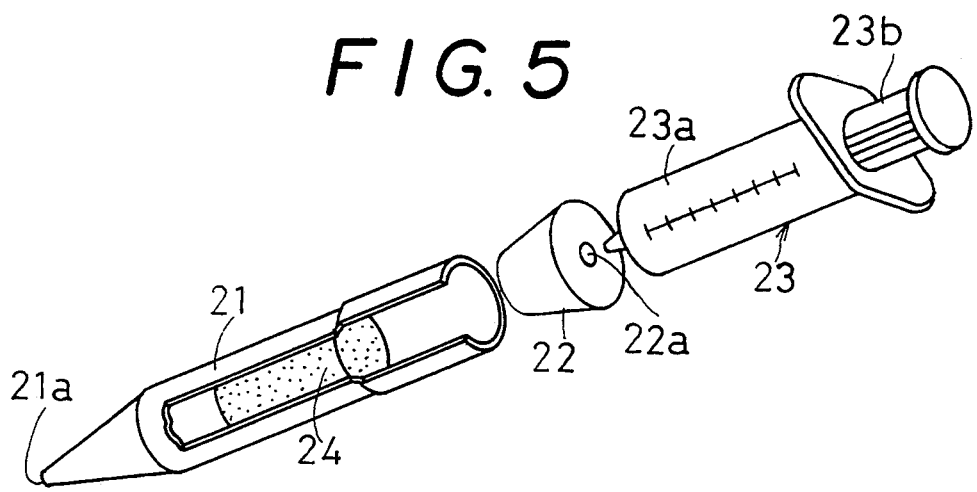
FIG. 5 is an exploded, perspective view of the fourth embodiment of the serum/plasma separating device according to this invention.
Figure 6:
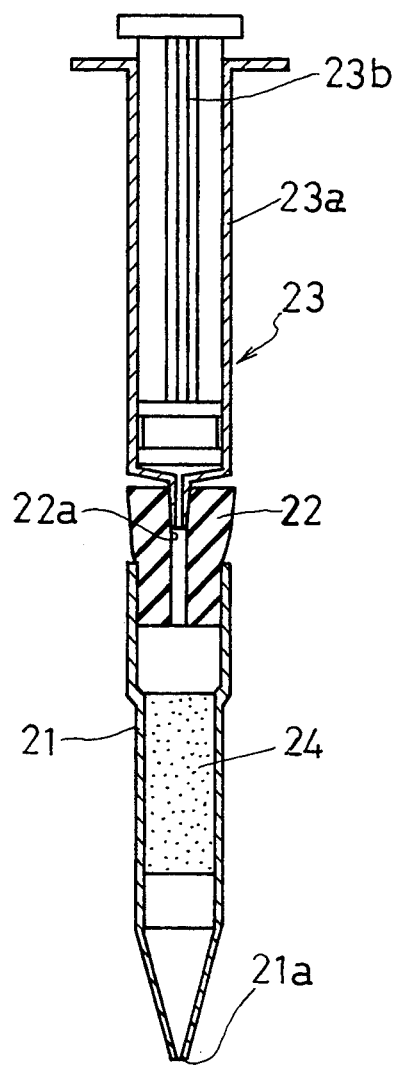
FIG. 6 is a sectional view of the fourth embodiment being assembled.

Referring to FIGS. 5 and 6, there is shown the forth embodiment of the separating device according to this invention. As illustrated, this separating device is built up of a hard column 21 made of resin or glass, which has a tapering tip portion or a blood sucking or ejecting port 21a, a rubber plug 22 fitted into an opening in the rear end of the column 21 and an injector 23 fitted into a through-hole 22a formed centrally through the rubber plug 22.

This injector 23 is used generally for collecting blood, and is made up of a cylinder 23a and a plunger 23b slidably inserted therein for vacuum suction or compression.

Within the column 21, there is fitted and fixed a filter form of blood cell separating layer 24.

This separating device is used as follows. When it is intended to collect blood in the cylinder 23a of the injector 23, the suction port 21a of the column 21 is first immersed in blood stored in other vessel, e.g., a test tube. Then, the plunger 23b is pulled out to suck the blood from the column 21 into the cylinder 23a. While the blood passes through the blood cell separating layer 24, the serum and plasma components are selectively separated from the blood and sucked in the cylinder 23a. The serum and plasma components may then be used for the required tests, if the injector 23 is pulled out of the rubber plug 22 to transfer the serum and plasma components to other sample vessel.

On the contrary, if the required amount of a blood sample stored in the cylinder 23a of the syringe 23 is ejected by the plunger 23b, it is then possible to feed only the serum and plasma components separated from the blood sample through the blood cell separating layer 24 in the column 21 to a sample vessel.

According to this method of using the separating device, blood can be collected directly from a human or animal subject with the injector 23 to which the needle is attached. Then, the needle is removed from the injector 23, which is in turn connected to the column 21 to give a push on the plunger 23, thereby obtaining the serum and plasma components. In other words, any vessel for storing blood after collecting the blood can be dispensed with, and the time of separation can be reasonably reduced as well.

Figure 7:
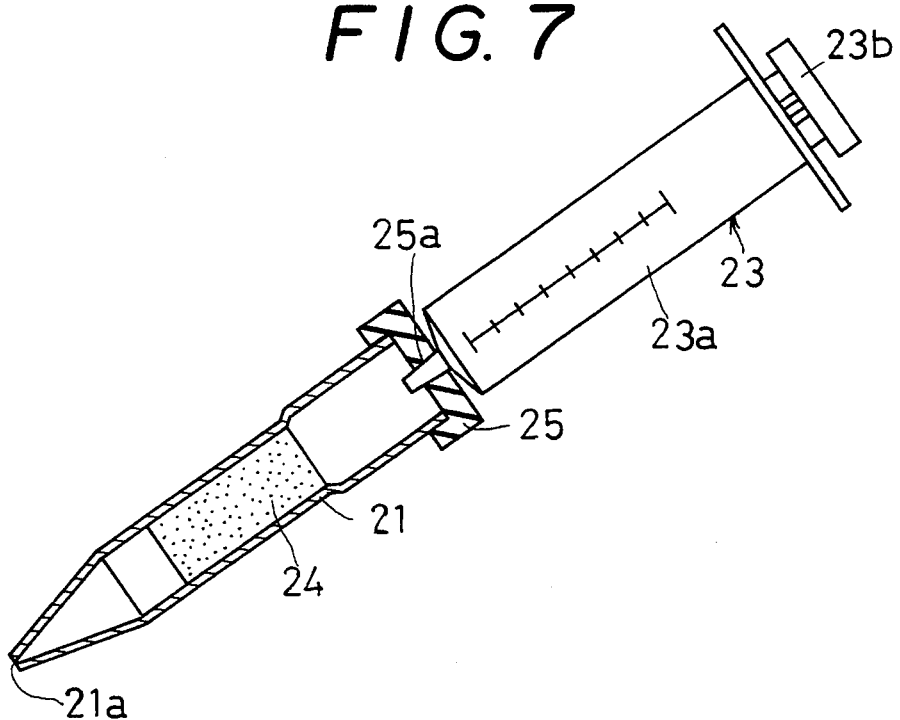
FIG. 7 is a sectional view of a modification of the fourth embodiment.

Referring to FIG. 7, there is shown a modification of the fourth embodiment. This embodiment is similar to the fourth embodiment with the exception that a rubber plug 25 having a larger diameter is fitted onto an opening in the rear end of a column 21 and the tip of an injector 23 is fitted into a hole 25a formed centrally in the plug 25. The manner of using this embodiment is similar to that of the fourth embodiment.

Figure 8:
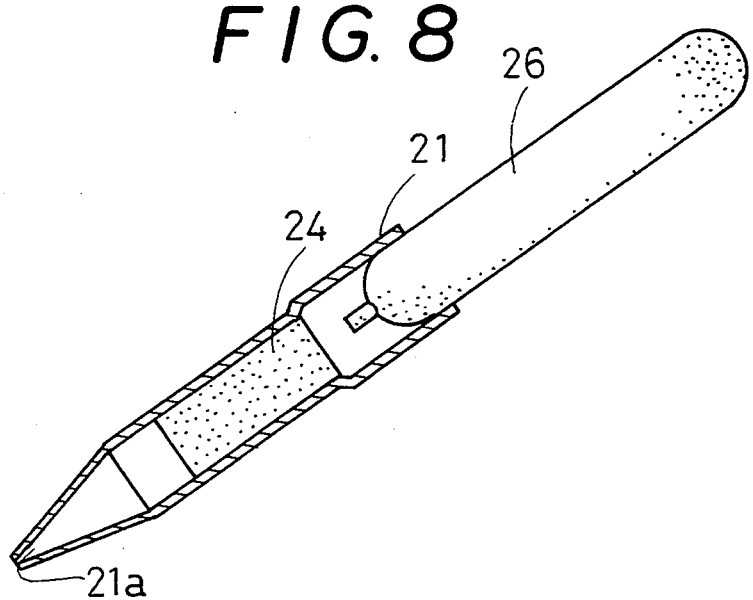
FIG. 8 is a sectional view of the fifth embodiment of the serum/plasma separating device according to this invention.

Referring to FIG. 8, there is shown the fifth embodiment of the separating device according to this invention. As illustrated, a syringe 26 is detachably received in an opening in the rear end of a column 21 provided therein with a blood cell separating layer 24.

This syringe 26 is formed of an elastic, flexible resin material, and has a volume sufficient for blood suction and ejection.

For use, the column 21 is connected to the syringe 26, as illustrated. While the syringe 26 is deflated, the suction port 21 in the column 21 is immersed in a blood sample vessel, so that the serum and plasma components can be sucked and collected in the syringe 26 by its elastic inflation. Alternatively, the syringe 26, in which a blood sample has previously been collected, is connected to the column 21, whereupon a push is given to the syringe 26 to eject the separated serum and plasma components from the ejecting port 21 in the column 21.

Figure 9:
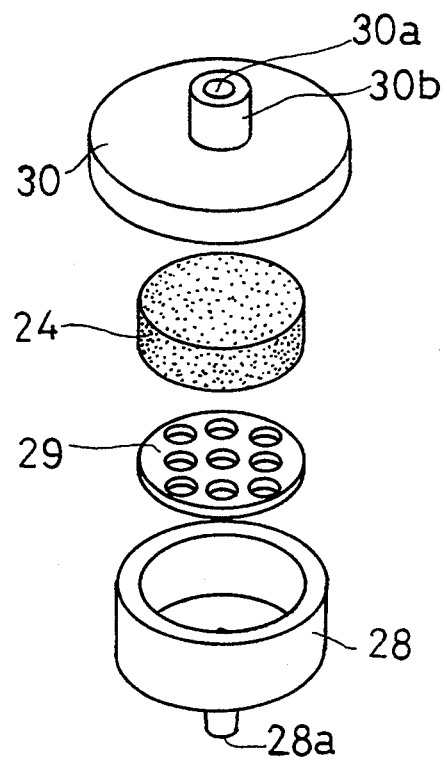
FIG. 9 is an exploded, perspective view of the sixth embodiment of the serum/plasma separating device according to this invention.
Figure 10:
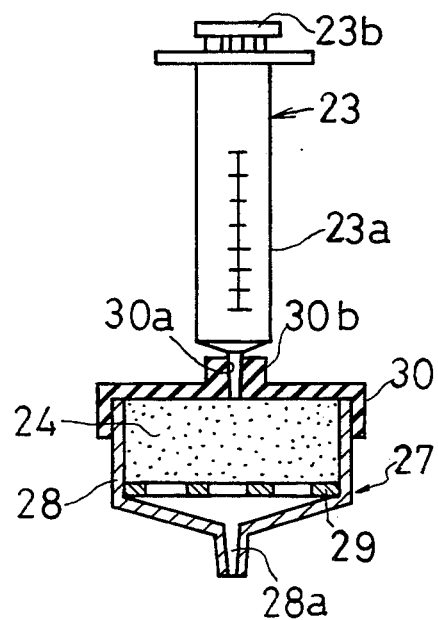
FIG. 10 is a sectional view of the sixth embodiment being assembled.

Referring to FIGS. 9 and 10, there is shown the sixth embodiment of the separating device according to this invention. As illustrated, a column 27 is built up of a funnel form of vessel 28 having a sucking or ejecting port 28a at the tip, a porous keep plate 29 located in the vessel 28, and a lid fitted over an opening in the rear portion of the vessel 28 and provided with a boss 30b having therein a through-hole 30a in communication with a cylinder 23a of an injector 23.

In the vessel 28, a blood cell separating layer 24 is sandwiched between the keep plate 29 and the lid 30, so that it is kept from movement during suction and ejection. Note that the manner of using this embodiment is similar to that of the fourth or fifth embodiment.

As explained above, the present invention enables the volume of serum and plasma required for as many as ten or more tests to be simply and inexpensively separated and recovered from a whole blood sample just after sampling, without posing some problems which are associated with separating procedures such as centrifuging. In addition, since serum and plasma can be separated from a blood sample just after sampling, high assay accuracy is achievable.

What is claimed is:

1. A process for separating and recovering serum and plasma components from a whole blood sample, which comprises passing said whole blood sample through a separating filter formed of a blood cell separating layer composed mainly of fibers impregnated with a coating agent wherein said blood cell separating layer is made up of glass fibers having an average diameter 0.5 to 2.5 $\mu$m and said coating agent comprises a polyacrylic ester derivative and polyethylene glycol.

2. A process as claimed in claim 1, wherein said polyacrylic ester derivative is selected from the group consisting of poly(butyl acrylate), poly(methyl acrylate) and poly(ethyl acrylate), and (a) poly(butyl acrylate), (b) poly(methyl acrylate) or poly(ethyl acrylate) and (c) polyethylene glycol are used in admixture at a ratio of (10–12):(1–4):(1–4).

* * * * *